(12) United States Patent
Kleyne

(10) Patent No.: US 7,524,511 B1
(45) Date of Patent: Apr. 28, 2009

(54) METHOD AND KIT FOR MOISTURIZING THE SURFACE OF THE EYE

(75) Inventor: Sharon F. Kleyne, Grants Pass, OR (US)

(73) Assignee: Rogue Valley Natural Springs, Inc., Grants Pass, OR (US)

( * ) Notice: Subject to any disclaimer, the term of this patent is extended or adjusted under 35 U.S.C. 154(b) by 1113 days.

(21) Appl. No.: 09/614,790

(22) Filed: Jul. 12, 2000

(51) Int. Cl.
- *A61K 8/02* (2006.01)
- *A61K 9/12* (2006.01)
- *A61K 33/00* (2006.01)
- *A61M 35/00* (2006.01)
- *A61M 15/00* (2006.01)
- *A62C 11/00* (2006.01)

(52) U.S. Cl. .................. 424/401; 424/43; 424/600; 604/294; 128/203.12; 239/333

(58) Field of Classification Search ............. 604/294; 424/78, 401, 606, 43, 600; 239/333; 128/203.12; 514/725

See application file for complete search history.

(56) References Cited

U.S. PATENT DOCUMENTS

| | | | |
|---|---|---|---|
| 4,753,945 A | | 6/1988 | Gilbard |
| 4,775,531 A | * | 10/1988 | Gilbard .................. 424/606 |
| 5,032,392 A | * | 7/1991 | Varma ..................... 424/78 |
| 5,294,607 A | | 3/1994 | Glonek |
| 5,307,095 A | * | 4/1994 | Ogura .................... 351/111 |
| 5,588,564 A | | 12/1996 | Hutson et al. |
| 5,620,663 A | * | 4/1997 | Aysta et al. ............... 422/104 |
| 5,627,611 A | * | 5/1997 | Scheiner .................. 351/158 |
| 5,881,956 A | * | 3/1999 | Cohen et al. ............. 239/333 |
| 5,893,515 A | | 4/1999 | Hahn et al. |
| 5,997,518 A | * | 12/1999 | Laibovitz et al. ......... 604/296 |
| 6,070,575 A | * | 6/2000 | Gonda et al. .......... 128/203.12 |
| 6,159,188 A | * | 12/2000 | Laibovitz et al. ......... 604/294 |

FOREIGN PATENT DOCUMENTS

| | | | |
|---|---|---|---|
| WO | WO-96/00050 | * | 1/1996 |
| WO | WO-97/23177 | * | 7/1997 |

OTHER PUBLICATIONS

Webster's II: New Riverside University Dictionary, 1984, Houghton Mifflin Company, p. 759.*
Schramm "selected terms in colloid and interface science," http://www.ucalgary.ca/~schramm/aerosols.htm.*
Records, RE, "The Tear Film", Chapter 3 of vol. 2 of Biomedical Foundations of Ophthalmology, Ed. William Tasman and Edward Jaeger, Lippincott Publishers (1993).
CCl Container/Aerosol Division brochure on Advanced Barrier System™ (1998).

\* cited by examiner

*Primary Examiner*—Shengjun Wang
(74) *Attorney, Agent, or Firm*—Howard Eisenberg, Esq.

(57) ABSTRACT

A method for moisturizing the eye in which an amount of aqueous fluid is administered to the eye in an amount below that which causes flooding of the eye and removal of the normal tear film from the surface of the eye. The fluid, when administered in accordance with the invention, rehydrates the already present tear film rather than replacing the tear film. A kit for moisturizing the eye in accordance with the invention is also disclosed.

9 Claims, 1 Drawing Sheet

METHOD AND KIT FOR MOISTURIZING THE SURFACE OF THE EYE

The invention pertains to the field of care and therapy of the surface of the eye, including the sclera, conjunctiva, and cornea. More particularly, the invention pertains to the application of therapeutic and other fluids for moisturizing and treating the surface of the eye.

BACKGROUND OF THE INVENTION

In normal situations, the surface of the eye, including the sclera, the conjunctiva, and the cornea, is kept moist by the presence of a tear film. This tear film is found in virtually all terrestrial vertebrates, with the exception of snakes.

The surface area of the eye in an adult human is about 2 $cm^2$. It is covered by a complex tear film having a trilaminar structure, with each of the layers having a discrete and necessary function.

Nearest to the surface of the eye is an inner layer of mucus approximately 10 to 20 μm in thickness. The mucus in this layer stabilizes the tear film and provides for attachment of the tear film to the underlying cornea and conjunctiva. The mucus also reduces the surface tension between the tear film and the eye and so permits the tear film to spread evenly across the eye.

The middle layer of the eye is an aqueous layer that is composed largely of water, electrolytes, and various proteins. This layer contains about 2 to 5 μl of aqueous fluid and forms the bulk of the tear film. Within this layer, pH, osmotic pressure, oxygen tension, and the levels of electrolytes such as potassium, calcium, chloride, inorganic phosphates, and acids such as lactic acid and citric acid, are maintained within narrow physiologic ranges. Proteins present in the aqueous layer of the tear film include albumin, and other proteins, such as immunoglobulins, interferon, β-lysin, and lysozyme which have antimicrobial activities.

Farthest from the surface of the eye is a lipid layer, which may range in thickness from a single monolayer to nearly 200 nm. Ordinarily, this layer is about 100 nm thick. This layer serves to retard evaporation of the tear film.

The tear film rapidly decreases in thickness following a blink. Without a subsequent blink, holes will begin to form in the tear film, called tear breakup, within about 30 seconds. Tear breakup times lower than 10 seconds are considered to be abnormal. This can occur with decreased tear formation or deficiencies in the mucus layer of the tear film. Other situations that can result in dryness of the eye surface include environmental aridity, contact lens wearing, and upon waking.

Typically, dryness of the eye is treated with water based solutions containing electrolytes and preservatives which maintain sterility of the solution for multiple applications. Solutions without preservatives are usually packaged in containers that provide for a single use, with disposal of the container and any residual solution following the single application.

The solutions are generally applied by drops, which provide about 20 to 25 μl of fluid to the eye surface. The application of eye drops results in rapid moisturizing of the eye. However, because the amount delivered is greater than the volume of the tear film, these drops have the disadvantage of flooding the eye, which washes away the tear film and replaces the tear film with the fluid that comprises the drops. Immediately following this flooding there exists a period of time when the normal tear film, with its three layer structure and the constituents of each layer, is not present on the eye surface. This can result in incomplete eye moisturizing which lasts for several blink cycles.

Other methods of administration of liquids onto the surface of the eye include eye cups, aerosol and pump sprays, and misters. Eye cups are used to bathe the surface of the eye in fluid, which results in flooding and washing away the tear film that is present on the eye surface. A mister that can be used to deliver a spray of droplets to the eye is described in Hahn, U.S. Pat. Nos. 5,346,132 and 5,893,515, each of which is incorporated herein by reference. In these patents, Hahn discloses several disadvantages of delivering fluid to the eye by drops, including difficulty in positioning the dropper and incomplete delivery of medications due to missing the eye and spilling onto the face. Hahn does not address the issue of the quantity of fluid that is administered to the eye or the issue of washing away the tear film due to flooding. The mister of Hahn delivers a measurable quantity of fluid and can be used for household or medical purposes or to moisturize the eyes or the skin.

Another mister is described in Hutson, U.S. Pat. No. 5,588,564, incorporated herein by reference. Like the mister of Hahn, the mister of Hutson can be used to deliver an adjustable and repeatable dose of fluid to the surface of the eye. Hutson does not address the issue of the quantity of fluid that is administered to the eye or the issue of washing away the tear film due to flooding.

A need exists for a method to moisturize the surface of the eye without flooding the eye or destroying the integrity of the natural tear film.

BRIEF SUMMARY OF THE INVENTION

It has been unexpectedly discovered that administering an amount of fluid to the surface of the eye at a level below that which results in flooding and washing away the tear film results in an improvement in eye moisturizing over prior art methods.

In one embodiment, the invention is a method for moisturizing the eye. The method according to the invention includes obtaining an applicator that can controllably deliver an aqueous fluid to the surface of the eye in a quantity below that which will flood the eye. In this manner, the method of the invention serves to rehydrate the aqueous layer of the tear film and leaves the normal trilaminar tear film intact. In accordance with the method of the invention, the quantity of fluid that is administered to the eye surface is less than about two times the volume of the normal aqueous layer of the tear film, that is less than about 10 μl. Preferably, between 0.5 and 6 μl is administered, and most preferably, between 2 and 5 μl is administered. The fluid may be administered to the eye surface in a single bolus, or may be administered over time, in ten seconds or less, preferably 5 seconds or less, in accordance with the invention.

The fluid may be delivered as drops, but is most preferably delivered as a fine mist. It has been discovered that aqueous fluids in the form of a fine mist are extremely well suited for rehydrating the aqueous portion of the tear film, without rinsing away the tear film.

In another embodiment, the invention is a kit for delivering a pharmaceutical composition for treating the eye, such as moisturizing the eye. In accordance with the invention, the kit contains an aqueous fluid pharmaceutical composition, a container that holds the pharmaceutical composition, and an applicator that, when actuated, controllably administers between about 0.5 and 50 μl of the pharmaceutical composition to a surface of about 2 $cm^2$ in about 10 seconds or less, preferably about 5 seconds or less. Preferably, the kit further contains instructions to controllably apply the pharmaceutical composition to the surface of the eye using the kit.

DETAILED DESCRIPTION OF THE INVENTION

Figure 1:
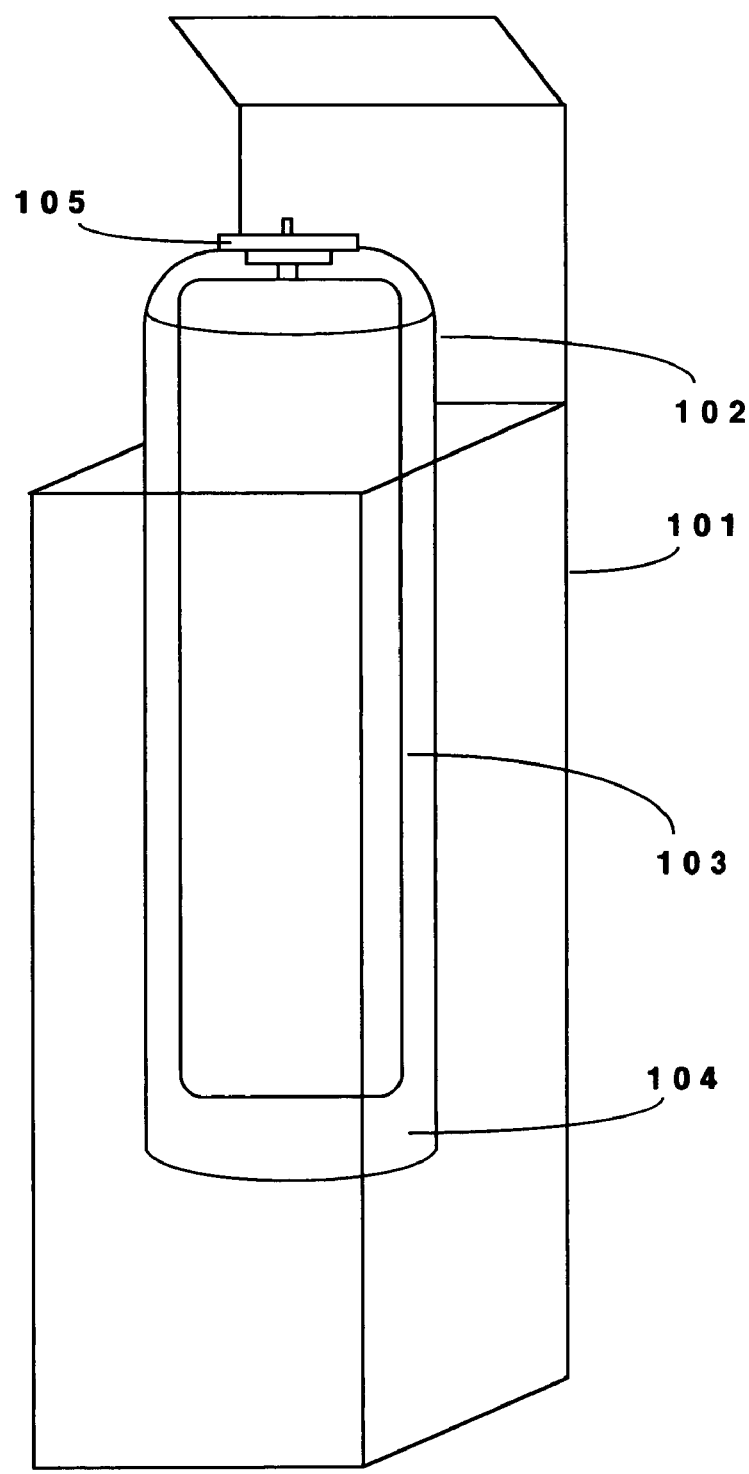
FIG. 1 shows one embodiment of the kit of the invention for moisturizing the eye in accordance with the method of the invention.

It has been discovered that a sudden increase in humidity to the tear film, as opposed to a splash of fluid such as occurs with presently available droppers and misters, increases the water content of the tear film while causing little or no displacement of the tear film.

In accordance with the invention, the volume of the tear film the surface of the eye is increased by applying a fluid in an amount not greater than about 100 to 200% of the volume of the aqueous portion of the tear film, which generally has a volume of 2 to 5 µl. Thus, in accordance with the invention, about 10 µl or less is applied to the surface of the eye. Preferably, 0.5 to 6 µl is applied, and most preferably 1 to 2 µl is applied, especially when moisturizing the eye because of the presence of dry eye, in which the total tear volume is typically between 1 to 2 µl. The volume of fluid in accordance with the invention acts to rehydrate the aqueous portion of the tear film and maintains the integrity of the overlying lipid and the underlying mucus layers.

In contrast with the present state of the art in which 20 to 50 µl of fluid is applied to the eye by dropper or by spray, the method in accordance with the invention reestablishes the normal state in individuals with dry eye. Present methods merely wash away the existing tear film and replace the tear film, or at least the middle aqueous layer, with an aqueous solution. These solutions lack the structure of the intact tear film and also differs from the normal aqueous layer of the tear film.

Generally, the above amount of fluid which is applied in accordance with the invention is applied during one blink cycle, that is between blinks. However, the fluid may be applied during a period of time in which one or more blinks occurs. Preferably, the fluid is applied within a period of 5 to 10 seconds or less.

Although the fluid may be administered in any form, including drops, dispersed droplets in air (mist), or a vapor, it is preferred that the fluid be administered in the form of a fine mist of discrete liquid droplets in which the average size of the fluid droplets is between about 5 and 150 microns in diameter. It has been found that a fine mist composed of droplets of this size range, preferably between about 0.1% to 1% of the tear volume per droplet, provides optimal hydration of the tear film and moisturization of the surface of the eye. Preferably, the average size of the fluid droplets is less than 100 microns, and more preferably less than 75 microns. Most preferably, the droplets have a diameter between 10 and 50 microns, with a most preferred range between 15 and 30 microns in diameter. Droplets above about 100 microns in diameter tend to incompletely vaporize and will fall out and produce undesirable wetting of the face and on horizontal surfaces. Droplets below about 20 microns in diameter are generally considered to be inhalable and can be aspirated into the upper and lower respiratory passages. This is acceptable when delivering a substance to the surface of the eye which is not potentially harmful to the respiratory system, such as a water. However, this may be undesirable when topical or ophthalmic medications are incorporated in the solution to be administered into the eye, when such medications may be irritating or toxic if inhaled.

The fluid that is delivered to the surface of the eye in accordance with the invention is a water based fluid. For moisturizing the eye, the fluid preferably is an aqueous fluid having a pH of neutral to slightly acidic, such as between about 7 to about 6.5. Preferably, the fluid has a low concentration of solutes, less than that of the normal tear film. In accordance with a preferred embodiment of the invention, the osmotic pressure of the fluid is less than 350 mOsm and most preferably less than 311 mOsm.

It is further preferred that the water be hypoallergenic and substantially free of preservatives and other chemical compounds that have a potential to irritate the surface of the eye.

The method of the invention may be used to deliver a therapeutic medication to the surface of the eye. Present methods of administration of medications to the eye use relatively large drops, about 20 µl or larger, to deliver the medication. This results in overflowing the eyelid margins with runoff of a portion of the medication to the surface of the face.

In accordance with the method of the invention, medication in an aqueous solution is applied to the surface of the eye, wherein the volume of the solution is less than about 10 µl. Preferably, the volume of the medication-containing-solution that is administered in accordance with the invention is between 0.5 and 6 µl, and most preferably between 2 and 5 µl. The solution containing the medication is preferably administered within about 5 to 10 seconds, and most preferably within one blink cycle, although the administration of the solution may be during the time of several blinks.

Any therapeutic medication that is soluble in water is suitable for the method of the invention. It is preferable that the medication not be irritating to the eye, although it is conceived that in some instances it may be desirable or necessary to administer therapeutic medications to the surface of the eye, even though the medications cause irritation. Examples of suitable therapeutic medications that are suitable for use in the method of the invention include antibiotics, including antibacterial, antifungal, and antiviral agents, sympathetic and parasympathetic agents, anti-glaucoma agents, and anti-inflammatory agents such as steroids.

In another embodiment, the invention is a kit for administering a controlled dosage of between 0.5 and less than 20 µl of an aqueous fluid to the surface of the eye. Preferably, the controlled dosage is less than 10 µl and most preferably less than 5 µl. In the most preferred embodiment, the controlled dosage is between 1 and 2 µl of fluid. In accordance with the invention, the kit contains a container, an aqueous fluid within the container, and an actuator that delivers a spray or fine mist of fluid in the dosage described above. It is preferred that the mist be composed of discrete droplets having an average size of about 5 to 150 microns in diameter, most preferably less than 100 microns, even more preferably less than 75 microns, most preferably less between 10 and 50 microns with a most preferred range between 15 and 30 microns in diameter. The kit may further contain instructions to apply the controlled dosage of the aqueous fluid to the surface of the eye. Preferably, the container of the kit is hermetically sealed so that it may be used for multiple applications of the aqueous fluid over several days to months without the need to include a preservative in the fluid.

A preferred embodiment of the kit of the invention is shown diagrammatically in FIG. 1. FIG. 1 shows a package such as a box 101 for containing a rigid, preferably metallic, hermetically sealed container 102, inside of which is an inner hermetically sealed flexible pouch 103, which contains a fluid to be dispensed. There is a pressurization agent such as compressed air or nitrogen 104 between the hermetically sealed container 102 and the flexible pouch 103, and an actuator 105 that permits the proper dosage of the fluid in the pouch 103 to escape when depressed. The kit further contains instructions (not shown) for delivering a pre-determined dosage of the fluid into the eye.

The invention is further described in the following non-limiting examples.

EXAMPLE 1

The volume of the tear film on the eyes of three adult human subjects is measured and determined to average 2.26 μl. The subjects are then treated by administering to surface of their eyes fine mist of between 50 and 100 micron average droplet size, with a total volume of between 2 to 5 μl within a period of 10 seconds per eye. Following administration, the tear volume is again measured and is determined to average 2.96 μl.

EXAMPLE 2

Samples of the tear film from three adult human subjects are obtained and subjected to HPLC chromatography to determine the baseline level of proteins and other constituents in the tear film. One eye from each of the subjects is then moisturized by administration of a standard drop of artificial tears of between 25 and 50 μl. Samples of the tear film from the three treated eyes are then obtained and subjected to HPLC chromatography. After obtaining the second group of samples, the opposite eye of each of the subjects is then moisturized by administration of the same artificial tears but in a fine mist made of droplets having a size between 50 and 100 microns for a total volume of about 5 μl. Samples of the tear film from the mist-treated eyes are then obtained and subjected to HPLC chromatography. The artificial tears are also subjected to HPLC chromatography.

The initial HPLC chromatography provides a profile of the constituents found in the normal tear film. It is found to contain various lipids, mucus, proteins, and electrolytes.

The HPLC chromatography following moisturization by a single large drop reveals that most if not all of the lipids and mucus remain in the tear film. The proteins and electrolytes that are present in the normal tear film are no longer present and the tear film has a chromatography profile similar to that of the artificial tears, minus the lipids and mucus.

The HPLC chromatography following moisturization by the fine mist reveals that the lipids and mucus remain in the tear film. The proteins and electrolytes that are present in the normal tear film are demonstrated by the chromatography to remain in the tear film following moisturization by the fine mist.

Further modifications, uses, and applications of the invention described herein will be apparent to those skilled in the art. It is intended that such modifications be encompassed in the following claims.

The invention claimed is:

1. A method for moisturizing the eye comprising spraying a mist consisting essentially of droplets of water having an average diameter between 5 and 150 microns on the surface of the eye of a subject in need thereof, wherein the amount of water that is sprayed on the eye is sufficient to hydrate the aqueous layer of the tear film on the eye of the subject but is below that which will wash away the tear film, and wherein the mist is sprayed from a device comprising a sealed container, water within said container, and an actuator for spraying a mist of water from said container, and wherein the water is sprayed on the surface of the eye within a period of 10 seconds.

2. The method of claim 1 wherein the subject is suffering from dry eye.

3. The method of claim 1 wherein proteins and electrolytes that were present in the tear film on the surface of the eye prior to the delivery of the aqueous fluid are present in the tear film following the delivery of the aqueous fluid to the surface of the eye as determined by high performance liquid chromatography (HPLC).

4. The method of claim 1 wherein the device further comprises a sealed flexible pouch containing said water within said container and a pressurization agent between said container and said pouch.

5. The method of claim 1 wherein the water is sprayed within a period of 5 seconds.

6. The method of claim 1 wherein less than about 10 μl is sprayed onto the surface of the eye.

7. The method of claim 1 wherein between about 0.5 and 6 μl is sprayed onto the surface of the eye.

8. The method of claim 1 wherein between about 2 and 5 μl is sprayed onto the surface of the eye.

9. The method of claim 1 wherein the subject is suffering from dryness of the eye.

* * * * *